(12) United States Patent
Wei (10) Patent No.: US 9,669,182 B2
(45) Date of Patent: Jun. 6, 2017

(54) NASAL JET AIRWAY

(75) Inventor: Huafeng Wei, Cherry Hill, NJ (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 915 days.

(21) Appl. No.: 13/387,316

(22) PCT Filed: Jul. 28, 2010

(86) PCT No.: PCT/US2010/043505
§ 371 (c)(1),
(2), (4) Date: Jan. 26, 2012

(87) PCT Pub. No.: WO2011/014543
PCT Pub. Date: Feb. 3, 2011

(65) Prior Publication Data
US 2012/0130264 A1    May 24, 2012

Related U.S. Application Data (60) Provisional application No. 61/229,131, filed on Jul. 28, 2009.

(51) Int. Cl.
| | | |
|---|---|---|
| *A61M 16/00* | (2006.01) | |
| *A61M 16/10* | (2006.01) | |
| *A61M 16/01* | (2006.01) | |
| *A61M 16/06* | (2006.01) | |
| *A61B 5/08* | (2006.01) | |

(52) U.S. Cl.
CPC ........ *A61M 16/10* (2013.01); *A61M 16/0096* (2013.01); *A61M 16/01* (2013.01); *A61M 16/0666* (2013.01); *A61M 16/0672* (2014.02); *A61B 5/082* (2013.01); *A61M 2202/0208* (2013.01); *A61M 2210/0618* (2013.01); *A61M 2230/432* (2013.01)

(58) Field of Classification Search
CPC .......... A61M 16/0666; A61M 16/0672; A61M 16/0461; A61M 16/0096; A61B 5/082
USPC ...................... 600/532; 128/207.18
See application file for complete search history.

(56) References Cited

U.S. PATENT DOCUMENTS

| | | | | |
|---|---|---|---|---|
| 4,270,530 | A * | 6/1981 | Baum | A61M 16/04 |
| | | | | 128/204.25 |
| 4,584,998 | A * | 4/1986 | McGrail | 128/207.15 |
| 5,456,250 | A * | 10/1995 | Hissong | 128/207.14 |
| 5,476,100 | A | 12/1995 | Galel | |
| 5,842,973 | A * | 12/1998 | Bullard | 600/194 |
| 6,098,617 | A * | 8/2000 | Connell | 128/200.26 |
| 6,131,571 | A | 10/2000 | Lampotang et al. | |
| 6,609,521 | B1 * | 8/2003 | Belani et al. | 128/207.14 |
| 7,273,050 | B2 * | 9/2007 | Wei | 128/200.26 |
| 7,278,420 | B2 * | 10/2007 | Ganesh | A61M 16/04 |
| | | | | 128/200.26 |
| 8,381,729 | B2 * | 2/2013 | Freitag et al. | 128/207.14 |

(Continued)

FOREIGN PATENT DOCUMENTS

WO    WO 2009144731 A2 * 12/2009    ........... A61M 16/04

*Primary Examiner* — Meredith Weare
(74) *Attorney, Agent, or Firm* — Mark S. Cohen; Pearl Cohen; Zedek Latzer Baratz LLP (57) ABSTRACT

The present invention provides an apparatus for nasally delivering a supraglottic jet ventilation and methods of treating breathing disorders by utilizing the apparatus for nasally delivering a supraglottic jet ventilation.

13 Claims, 2 Drawing Sheets

(56) References Cited

U.S. PATENT DOCUMENTS

| | | | |
|---|---|---|---|
| 2004/0129272 A1* | 7/2004 | Ganesh | A61M 16/04 128/207.14 |
| 2004/0215061 A1 | 10/2004 | Kimmel et al. | |
| 2005/0279360 A1* | 12/2005 | Wei | 128/207.14 |
| 2008/0135044 A1* | 6/2008 | Freitag et al. | 128/200.26 |
| 2009/0277447 A1* | 11/2009 | Voss et al. | 128/204.18 |
| 2011/0098592 A1* | 4/2011 | Colman | A61M 16/0463 600/532 |

* cited by examiner

NASAL JET AIRWAY

CROSS-REFERENCE TO RELATED APPLICATIONS

This application is a National Phase Application of PCT International Application No. PCT/US10/43505, International Filing Date Jul. 28, 2010, claiming priority of U.S. Provisional Patent Application, 61/229,131, filed Jul. 28, 2009.

FIELD OF THE INVENTION

The invention provides an apparatus for nasally delivering a supraglottic jet ventilation and methods of using the same.

BACKGROUND OF THE INVENTION

Respiratory depression or "labored breathing" is frequently seen in patients with various kinds of diseases. Oxygen is usually provided to patients either through noses or mouths to improve the oxygenation and correct hypoxia. However, in patients with severe respiration depression or apnea, simple inhalation of oxygen via the nose or mouth may not be adequate or impossible and result in hypoxia and/or hypercapnia. Tracheal intubation and mechanical ventilation can help patient's breath.

However, tracheal intubation is invasive and may have multiple complications related to tracheal intubation (e.g. requirement of significant level of sedation, airway damage, failed intubation in a difficult airway and troubles to wean from the ventilators).

Heavy sedations with intravenous infusion of general anesthetic propofol are frequently used to assist outpatient procedures (e.g. endoscope examinations of gastrointestinal tracts or bile ducts, bronchoscope etc.). Propofol sedation can depress patient's breathing severely especially when patient is on prone position. Inhalation of oxygen via nose or mouth with patient's natural breathing is often not adequate to correct hypoxia and/or hypercapnia.

Mask ventilation is often impossible because of the endoscope in the mouth. Tracheal intubations and mechanical ventilation are usually not chosen because these procedures are often short and do not warrant full general anesthesia.

Hypoxia during tracheal intubation is the most common complication causing morbidity and mortality in the clinical practice of anesthesia, which is often related to an unexpected difficult airway. Occasionally, both mask ventilation and tracheal intubation are impossible in an apnea patient resulting in non-ventilation and non-intubation airway emergency. Lack of an effective airway device that maintains oxygenation and ventilation during the process of tracheal intubation in an apnea patient contribute to the morbidity and mortality. It is lifesaving if oxygen can be provided to a patient and adequate oxygen levels maintained at this time.

SUMMARY OF THE INVENTION

In one embodiment, the present invention provides an apparatus for nasally delivering a supraglottic jet ventilation, comprising: a. an elongated flexible tube having: i. an annular cylindrical wall defining at least one tube lumen extending substantially the entire length thereof, a cylindrical wall having external and internal surfaces and having proximal and distal ends, ii. a first catheter lumen extending lengthwise within a cylindrical wall between an external surface and an internal surface and along a dorsal region thereof, the first lumen having a first opening through the external surface of a cylindrical wall adjacent the proximal end thereof and a second opening through the internal surface of a cylindrical wall adjacent the distal end thereof, iii. a second catheter lumen extending lengthwise within the cylindrical wall along a ventral region thereof, the lumen having a first opening through the external surface of the cylindrical wall adjacent the proximal end thereof and a second opening through a distal face of the aid cylindrical wall at the distal end of the cylindrical wall; b. a first catheter extending dorsally through the first catheter lumen, the first catheter having a proximal end extending outside of the cylindrical wall through the first opening and having a distal end extending into the tube lumen through the second opening; and c. a second catheter ventrally through the first catheter lumen, the second catheter having a proximal end extending outside of the cylindrical wall through the first opening and having a distal end extending through the second opening.

In another embodiment, the present invention further provides a method of ventilating a subject afflicted with a pathology resulting in compromised breathing, comprising the steps of: a. within a nasal airway of a subject, positioning an apparatus for nasally delivering a jet of air or oxygen at various concentrations: an elongated flexible tube having a proximal end, a distal end, an external surface, an internal surface and a wall portion defining at least one lumen extending substantially the entire length of the tube, an opening through the external surface of the tube located dorsally adjacent the proximal end, an opening through the internal surface of the tube located dorsally adjacent the distal end and a lumen therebetween, an opening through the external surface of the tube located ventrally adjacent the proximal end, an opening through the wall portion of the tube located ventrally adjacent to the distal end and a lumen therebetween; a jet catheter extending between the dorsally located external opening and dorsally located internal opening, the first catheter having a proximal end and a distal end, wherein the proximal end is extending from the dorsally located external opening; and a $CO_2$ monitoring catheter extending between the ventrally located opening and wall portion opening, the second catheter having a proximal end and a distal end, wherein the proximal end is extending from the ventrally located external opening; and b. Initiating jet ventilation through the jet catheter tube or $CO_2$ monitoring catheter using a jet ventilator or device.

In another embodiment, the present invention further provides a system for ventilating a subject afflicted with a pathology resulting in compromised breathing, comprising: an apparatus for nasally delivering a jet of air or oxygen at different concentrations, comprising: i. an elongated flexible tube having: 1. an annular cylindrical wall defining at least one tube lumen extending substantially the entire length thereof, the cylindrical wall having external and internal surfaces and having proximal and distal ends, 2. a first catheter lumen, extending lengthwise within the cylindrical wall between the external surface and the internal surface and along a dorsal region thereof, the first lumen having a first opening through the external surface of the cylindrical wall adjacent the proximal end thereof and a second opening through the internal surface of the cylindrical wall adjacent the distal end thereof, 3. a second catheter lumen extending lengthwise within the cylindrical wall along a ventral region thereof, the lumen having a first opening through the external surface of the cylindrical wall adjacent the proximal end thereof and a second opening through the internal surface adjacent to a distal end of the cylindrical wall; i. a first catheter adapted to deliver a jet pulse or to monitor end-tidal $CO_2$ extending dorsally through the first catheter lumen, the first catheter having a proximal end extending outside of the cylindrical wall through the first opening and having a distal end extending into the tube lumen through the second opening; and ii. a second catheter adapted for monitoring $CO_2$ levels or for providing jet ventilation ventrally through the first catheter lumen, the second catheter having a proximal end extending outside of the cylindrical wall through the first opening and having a distal end extending through the second opening; b. a jet ventilator or device; and c. a $CO_2$ monitoring device.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 2. is an embodiment of the device: a nasal airway unit (1) comprising: a tube (7) having a proximate end (9), a distal end (6), an anterior surface (10), and a posterior surface (11), a first tube wall (15) and a second tube wall (16) enclosing a tube lumen (8); a jet catheter (4) partially enclosed within the first tube wall (15) having proximate end (12), a distal end (5) and comprising a first jet catheter wall and a second jet catheter wall (13 and 17, respectively) enclosing a jet catheter lumen (14), a proximate end (12) of jet catheter extends outwards from the first tube wall (15), and the distal end (5) of jet catheter extends inwards from the first tube wall (15) into the tube lumen; an end-tidal $CO_2$ monitoring catheter (2), partially enclosed within the second tube wall (16) having proximate end (18), a distal end (3) and comprising a first end-tidal $CO_2$ monitoring catheter wall and a second end-tidal $CO_2$ monitoring catheter wall (19, 20) enclosing an end-tidal $CO_2$ monitoring catheter lumen (21), wherein the proximate end (18) of an end-tidal $CO_2$ monitoring catheter extends outwards from the second tube wall (16), wherein the distal end (3) of an end-tidal $CO_2$ monitoring catheter is located within the second tube wall (16).

DETAILED DESCRIPTION OF THE INVENTION

In one embodiment, the present invention provides an apparatus for nasally delivering a supraglottic jet ventilation, comprising: a. an elongated flexible tube having: i. an annular cylindrical wall defining at least one tube lumen extending substantially the entire length thereof, a cylindrical wall having external and internal surfaces and having proximal and distal ends, ii. a first catheter lumen extending lengthwise within a cylindrical wall between an external surface and an internal surface and along a dorsal region thereof, the first lumen having a first opening through the external surface of a cylindrical wall adjacent the proximal end thereof and a second opening through the internal surface of a cylindrical wall adjacent the distal end thereof, iii. a second catheter lumen extending lengthwise within the cylindrical wall along a ventral region thereof, the lumen having a first opening through the external surface of the cylindrical wall adjacent the proximal end thereof and a second opening through a distal face of the aid cylindrical wall at the distal end of the cylindrical wall; b. a first catheter extending dorsally through the first catheter lumen, the first catheter having a proximal end extending outside of the cylindrical wall through the first opening and having a distal end extending into the tube lumen through the second opening; and c. a second catheter ventrally through the first catheter lumen, the second catheter having a proximal end extending outside of the cylindrical wall through the first opening and having a distal end extending through the second opening.

Figure 1:
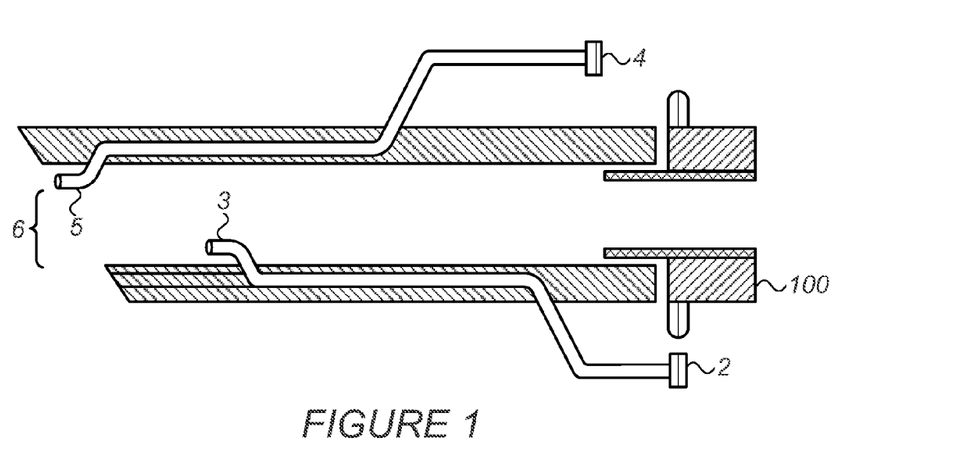
FIG. 1. is a schematic drawing of the Device. 1. Proximal end of the jet nasal airway (away from the patient's vocal cords) and an adaptor for connecting to conventional mechanical ventilation; 2. Distal end of the built-in end-tidal $CO_2$ monitoring catheter/jet catheter; 3. Proximal end of the built-in end-tidal $CO_2$ monitoring catheter/jet catheter; 4. Distal end of the built-in jet catheter/end-tidal $CO_2$ monitoring catheter; 5. Distal end of the built-in jet catheter/end-tidal $CO_2$ monitoring catheter; 6. Distal end of the jet nasal airway (close to the patient's vocal cords). Proposed length of jet nasal airway is 2-20 cm. Proposed ID and OD for nasal jet airway is 1-10 mm and 2-12 mm respectively. Proposed ID for jet catheter or end-tidal $CO_2$ monitoring catheter is 0.1-2.5 mm. Jet catheter can be used as an end-tidal $CO_2$ monitoring catheter and vice versa depending on the condition to achieve maximum chest rise and end-tidal $CO_2$. The position of 5 can be on any part of an inner surface of 15. Position of 3 and 5 can be exchanged (e.g. 3 and 5 can be on either anterior or posterior wall of the jet nasal airway).

In another embodiment, the present invention provides that an apparatus for nasally delivering a supraglottic jet ventilation is a device of the invention. In another embodiment, the present invention provides that an apparatus for nasally delivering a supraglottic jet ventilation comprises (see FIG. 1) proximal end of the jet nasal airway (away from the patient's vocal cord) and an adaptor for connecting to conventional mechanical ventilation (100); proximal end of the built-in end-tidal $CO_2$ monitoring catheter/jet catheter (2); distal end of the built-in end-tidal $CO_2$ monitoring catheter/jet catheter (3); proximal end of the built-in jet catheter/end-tidal $CO_2$ monitoring catheter (4); distal end of the built-in jet catheter/end-tidal $CO_2$ monitoring catheter (5); proximal end of the jet nasal airway (close to the patient's vocal cord)(6). In another embodiment, the present invention provides that the length of jet nasal airway is 2-20 cm. In another embodiment, the present invention provides that the length of jet nasal airway is 2-5 cm. In another embodiment, the present invention provides that the length of jet nasal airway is 4-10 cm. In another embodiment, the present invention provides that the length of jet nasal airway is 10-20 cm. In another embodiment, the present invention provides that the ID and OD for nasal jet airway are 1-10 mm and 2-12 mm respectively. In another embodiment, the present invention provides that the ID for jet catheter or end-tidal $CO_2$ monitoring catheter is 0.1-2.5 mm. In another embodiment, the present invention provides that the jet catheter is used as an end-tidal $CO_2$ monitoring catheter and vice versa depending on the condition to achieve maximum chest rise and end-tidal $CO_2$.

In another embodiment, the first catheter is adapted to accommodate a jet ventilator. In another embodiment, the first catheter is adapted to accommodate a jet device. In another embodiment, the first catheter is adapted to accommodate an oxygen insufflation. In another embodiment, the first catheter is adapted to accommodate a $CO_2$ monitoring means.

In another embodiment, the second catheter is adapted to monitor $CO_2$. In another embodiment, the second catheter is adapted to accommodate a jet ventilator. In another embodiment, the second catheter is adapted to accommodate a jet device. In another embodiment, the second catheter is adapted to accommodate an oxygen insufflation.

In another embodiment, the cross-sectional area of the jet catheter lumen is smaller than the cross-sectional area of the tube lumen. In another embodiment, the jet catheter extends to the point adjacent the distal end of the tube. In another embodiment, the jet catheter lumen has a cross-sectional area of between about 0.1 mm and 2.5 mm. In another embodiment, the $CO_2$ monitoring catheter lumen has a cross-sectional area of between about 0.1 mm and 2.5 mm. In another embodiment, the tube lumen has a cross-sectional area of between about 1 mm and 10 mm. In another embodiment, the apparatus further comprises a visual monitoring means for observing the vocal cord. In another embodiment, the visual monitoring means is positioned within said tube lumen. In another embodiment, the apparatus further comprises a jet ventilation source for providing jet ventilation through the jet catheter and/or $CO_2$ monitoring catheter. In another embodiment, the apparatus have a length of between about 2 and 20 cm. In another embodiment, the jet ventilation source is controlled for jet pulse frequency, pulse pressure, inspiratory/expiratory ratio (UE) ratio, and the oxygen concentrations in the jet pulse.

In another embodiment, the present invention further provides a method of ventilating a subject afflicted with a pathology resulting in compromised breathing, comprising the steps of: a. within a nasal airway of a subject, positioning an apparatus for nasally delivering a jet of air or oxygen at various concentrations: an elongated flexible tube having a proximal end, a distal end, an external surface, an internal surface and a wall portion defining at least one lumen extending substantially the entire length of the tube, an opening through the external surface of the tube located dorsally adjacent the proximal end, an opening through the internal surface of the tube located dorsally adjacent the distal end and a lumen therebetween, an opening through the external surface of the tube located ventrally adjacent the proximal end, an opening through the wall portion of the tube located ventrally adjacent the distal end and a lumen therebetween; a jet catheter extending between the dorsally located external opening and dorsally located internal opening, the first catheter having a proximal end and a distal end, wherein the proximal end is extending from the dorsally located external opening; and a $CO_2$ monitoring catheter extending between the ventrally located opening and wall portion opening, the second catheter having a proximal end and a distal end, wherein the proximal end is extending from the ventrally located external opening; and b. Initiating jet ventilation through the jet catheter tube or $CO_2$ monitoring catheter using a jet ventilator or device.

In another embodiment, the method further comprises the step of adjusting the position of the jet pulse in the nasal airway to obtain the maximum end-tidal $CO_2$ with a capnogram having a stable plateau. In another embodiment, the method further comprises the step of observing the patient's vocal cord(s) by at least one visual monitoring means. In another embodiment, the visual monitoring means is laryngoscope or a regid laryngoscope or a fiber-optic scope.

In another embodiment, the method further comprises the step of changing jet ventilation through the jet catheter to the $CO_2$ monitoring catheter, and using jet catheter for $CO_2$ monitoring. In another embodiment, the choice of the catheter function depends on best chest rise and maximum end-tidal $CO_2$ obtained with use of each of two catheters.

In another embodiment, the method further comprises the step of capping the proximal end of the jet catheter. In another embodiment, the method further comprises the step of capping the proximal end of the $CO_2$ monitoring catheter. In another embodiment, the method further comprises the step of providing conventional ventilation using a breathing bag to the subject through the first tube. In another embodiment, the method further comprises the step of delivering medication to the subject through the jet catheter. In another embodiment, the method further comprises the step of delivering medication to the subject through the $CO_2$ monitoring catheter. In another embodiment, the method further comprises the step of applying suction forces to the nasal airway in a subject through the jet catheter or $CO_2$ monitoring catheter.

In another embodiment, the pathology is respiratory depression, apnea, hypoxia, hypercapnia, or any combination thereof, or during the placement and/or removal of an oral and/or nasal endotracheal tube.

In another embodiment, the present invention further provides a system for ventilating a subject afflicted with a pathology resulting in compromised breathing, comprising: an apparatus for nasally delivering a jet of air or oxygen at different concentrations, comprising: i. an elongated flexible tube having: 1. an annular cylindrical wall defining at least one tube lumen extending substantially the entire length thereof, the cylindrical wall having external and internal surfaces and having proximal and distal ends, 2. a first catheter lumen, extending lengthwise within the cylindrical wall between the external surface and the internal surface and along a dorsal region thereof, the first lumen having a first opening through the external surface of the cylindrical wall adjacent the proximal end thereof and a second opening through the internal surface of the cylindrical wall adjacent the distal end thereof, 3. a second catheter lumen extending lengthwise within the cylindrical wall along a ventral region thereof, the lumen having a first opening through the external surface of the cylindrical wall adjacent the proximal end thereof and a second opening through the internal surface adjacent to a distal end of the cylindrical wall; i. a first catheter adapted to deliver a jet pulse or to monitor end-tidal $CO_2$ extending dorsally through the first catheter lumen, the first catheter having a proximal end extending outside of the cylindrical wall through the first opening and having a distal end extending into the tube lumen through the second opening; and ii. a second catheter adapted for monitoring $CO_2$ levels or for providing jet ventilation ventrally through the first catheter lumen, the second catheter having a proximal end extending outside of the cylindrical wall through the first opening and having a distal end extending through the second opening; b. a jet ventilator or device; and c. a $CO_2$ monitoring device.

In another embodiment, the system further comprises means for viewing a vocal chord. In another embodiment, the jet ventilator is any device that generates jet pulses. In another embodiment, the $CO_2$ monitoring means is capable of monitoring end-tidal $CO_2$. In another embodiment, the means of viewing vocal cords is a fiber optic scope.

In another embodiment, the system further comprises means for applying suction to the apparatus through the tube lumen. In another embodiment, the system further comprises central control means. In another embodiment, the central control means comprises a sensor of breathing, a computer to integrate breathing signal and provide triggering signal for jet ventilator to synchronize the jet pulse from jet ventilator with spontaneous breathing of subject.

In another embodiment, provided herein a jet nasal airway device (FIG. 2) comprising a nasal airway unit (1) comprising: a tube (7) having a proximate end (9), a distal end (6), an anterior surface (10), and a posterior surface (11), a first tube wall (15) and a second tube wall (16) enclosing a tube lumen (8); a jet catheter (4) partially enclosed within the first tube wall (15) having proximate end (12), a distal end (5) and comprising a first jet catheter wall and a second jet catheter wall (13 and 17, respectively) enclosing a jet catheter lumen (14), wherein the proximate end (12) of jet catheter extends outwards from the first tube wall (15), wherein the distal end (5) of jet catheter extends inwards from the first tube wall (15) into the tube lumen; an end-tidal $CO_2$ monitoring catheter (2), partially enclosed within the second tube wall (16) having proximate end (18), a distal end (3) and comprising a first end-tidal $CO_2$ monitoring catheter wall and a second end-tidal $CO_2$ monitoring catheter wall (19, 20) enclosing an end-tidal $CO_2$ monitoring catheter lumen (21), wherein the proximate end (18) of an end-tidal $CO_2$ monitoring catheter extends outwards from the second tube wall (16), wherein the distal end (3) of an end-tidal $CO_2$ monitoring catheter is located within the second tube wall (16).

In another embodiment, the proximal end of the end-tidal $CO_2$ monitoring catheter is capped. In another embodiment, the proximal end of the end-tidal $CO_2$ monitoring catheter is cuffed. In another embodiment, the proximal end of the jet catheter is capped. In another embodiment, the proximal end of the jet catheter is cuffed.

In another embodiment, the terms "apparatus for nasally delivering a jet of air" and "Jet nasal airway device" are used interchangeably.

In another embodiment, the proximal end of the $CO_2$ monitoring catheter is capped. In another embodiment, the proximal end of the $CO_2$ monitoring catheter is cuffed. In another embodiment, the proximal end of the jet catheter is capped. In another embodiment, the proximal end of the jet catheter is cuffed.

In another embodiment, the first catheter is adapted to accommodate an air jet. In another embodiment, the second catheter is adapted to monitor $CO_2$. In another embodiment, the second catheter is an end-tidal $CO_2$ monitoring catheter.

Figure 2:
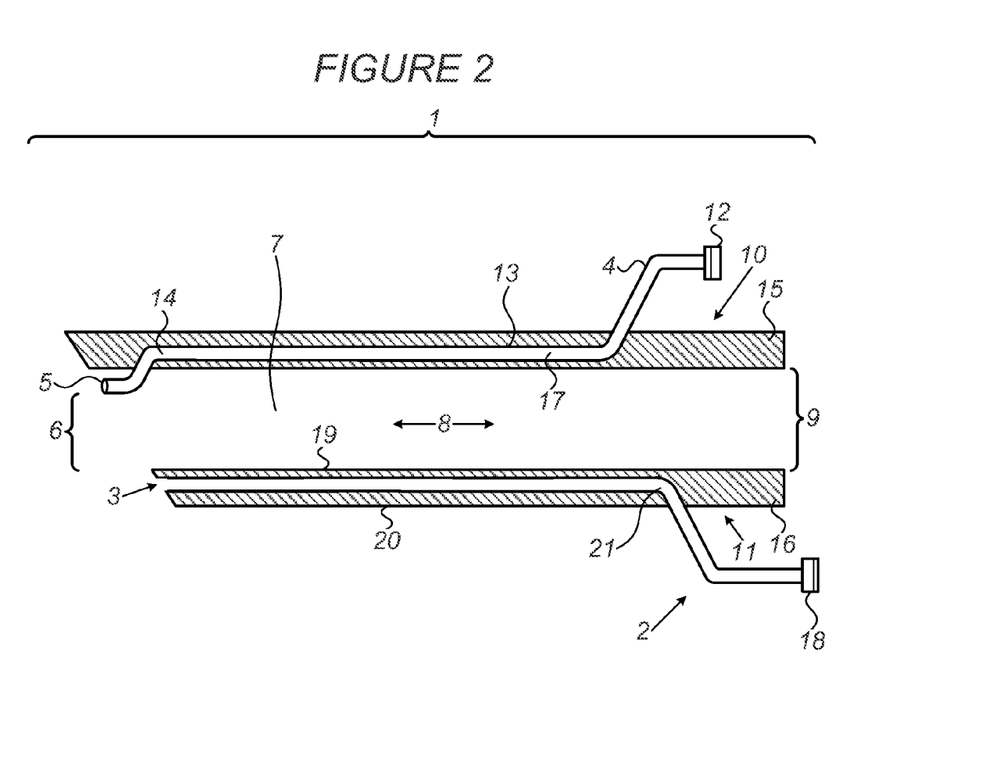

In another embodiment, the cross-sectional area of the jet catheter lumen is smaller than the cross-sectional area of the tube lumen. In another embodiment, the jet catheter extends beyond the distal end of the tube. In another embodiment, the first tube wall (15) has a protruding end. In another embodiment, the second tube wall (16) has a protruding end.

In another embodiment, the jet catheter lumen (14) has a cross-sectional area of 0.1 mm to 4 mm. In another embodiment, the jet catheter lumen has a cross-sectional area of 0.5 mm to 1.5 mm. In another embodiment, the jet catheter lumen has a cross-sectional area of 0.11 mm to 2.5 mm. In another embodiment, the jet catheter lumen has a cross-sectional area of 1 mm to 3 mm. In another embodiment, the jet catheter lumen has a cross-sectional area of 2.5 mm to 3.5 mm. In another embodiment, the jet catheter lumen has a cross-sectional area of 2.5 mm to 4 mm.

In another embodiment, the end-tidal $CO_2$ monitoring catheter (21) has a cross-sectional area of 0.1 mm to 4 mm. In another embodiment, the end-tidal $CO_2$ monitoring catheter has a cross-sectional area of 0.5 mm to 1.5 mm. In another embodiment, the end-tidal $CO_2$ monitoring catheter has a cross-sectional area of 0.1 mm to 2.5 mm. In another embodiment, the end-tidal $CO_2$ monitoring catheter has a cross-sectional area of 1 mm to 3 mm. In another embodiment, the end-tidal $CO_2$ monitoring catheter has a cross-sectional area of 2.5 mm to 3.5 mm. In another embodiment, the end-tidal $CO_2$ monitoring catheter has a cross-sectional area of 2.5 mm to 4 mm.

In another embodiment, the tube's lumen has a cross-sectional area of 1 mm to 12 mm. In another embodiment, the tube's lumen has a cross-sectional area of 1 mm to 9 mm. In another embodiment, the tube's lumen has a cross-sectional area of 1 mm to 3 mm. In another embodiment, the tube's lumen has a cross-sectional area of 2 mm to 4 mm. In another embodiment, the tube's lumen has a cross-sectional area of 3 mm to 5 mm. In another embodiment, the tube's lumen has a cross-sectional area of 4 mm to 6 mm. In another embodiment, the tube's lumen has a cross-sectional area of 5 mm to 7 mm. In another embodiment, the tube's lumen has a cross-sectional area of 6 mm to 8 mm. In another embodiment, the tube's lumen has a cross-sectional area of 7 mm to 9 mm. In another embodiment, the tube's lumen has a cross-sectional area of 3 mm to 8 mm. In another embodiment, the tube's lumen has a cross-sectional area of 2 mm to 5 mm. In another embodiment, the tube's lumen has a cross-sectional area of 6 mm to 9 mm.

In another embodiment, the jet nasal airway device further comprises a visual monitoring means for observing the vocal cord. In another embodiment, the visual monitoring means comprises an optic fiber.

In another embodiment, the visual monitoring means is attached to the jet nasal airway device. In another embodiment, the visual monitoring means is comprised within the jet nasal airway device. In another embodiment, the visual monitoring means is positioned within the tube's lumen.

In another embodiment, the jet nasal airway device further comprises a bendable, shape-retaining stylet for shaping the jet nasal airway device. In another embodiment, the jet nasal airway device is compressible. In another embodiment, the jet nasal airway device is flexible. In another embodiment, the jet nasal airway device is elastic.

In another embodiment, the terms "apparatus for nasally delivering a jet of air" and a "jet nasal airway device" are used interchangeably. In another embodiment, the jet nasal airway device further comprises a jet ventilation source for providing jet ventilation through the jet catheter. In another embodiment, the jet nasal airway device further comprises an inflatable insufflation cuff.

In another embodiment, the jet nasal airway device of have a length of 2-20 mm. In another embodiment, the jet nasal airway device of have a length of 2-5 mm. In another embodiment, the jet nasal airway device of have a length of 4-8 mm. In another embodiment, the jet nasal airway device of have a length of 5-10 mm. In another embodiment, the jet nasal airway device of have a length of 8-12 mm. In another embodiment, the jet nasal airway device of have a length of 10-15 mm. In another embodiment, the jet nasal airway device of have a length of 12-20 mm.

In another embodiment, the device is an implantable device that is positioned within an anatomical cavity of the nose. In another embodiment, the device is an implantable device that is positioned within the anatomical cavity of the nose.

In another embodiment, the device is comprised of a biocompatible material. In another embodiment, the device is comprised of a combination of biocompatible materials. In another embodiment, the device is comprised of a biocompatible material that provides the necessary physical properties for the device of the invention. In another embodiment, the device is comprised of a polymeric material (both natural and synthetic), a polymeric fiber, a ceramic material, a composite material, a metal, a metal oxide, and combinations thereof. In another embodiment, the device is comprised of amylose and amylopectin derivatives, polyamides, polyvinyl alcohol, polyvinyl acetals, polyvinylpyrrolidone, polyacrylates, epoxy resins, and polyurethanes (mixtures thereof, blends with other ingredients, or copolymers thereof) and combinations thereof.

In another embodiment, the device is coated. In another embodiment, the device is coated with a polymer or coating composition. In another embodiment, the device is coated with hyaluronic acid. In another embodiment, the device is coated with Perylenem™. In another embodiment, the device is coated with heparin. In another embodiment, the device is coated with a lubricant. In another embodiment, the device is coated with a thrombo-prevention compound. In another embodiment, the device is coated with an anti-bacterial compound. In another embodiment, the device is coated with an anti-inflammatory compound. In another embodiment, the device is cross-linked or bound to a drug by gamma irradiation, chemical binding (as with binder or crosslinking molecules such as N-hydroxysuccinimide), or any other method. In another embodiment, the device is capable of the controlled release of a drug such as a surfactant, lubricant, antibiotic, anti-acid, antifungal agent, anti-inflammatant, or the like.

In another embodiment, the device is formed in part or in whole from a number of materials. In another embodiment, the materials are typically selected so as to ensure optimal device performance given the particular construction and/or geometry of the device. In another embodiment, the materials are tailored to the environment conditions to which the device may be exposed. In another embodiment, the environmental conditions of the nose may vary according to a number of factors, e.g., the particular temperature of the animal whose nose is to receive the device, whether the animal is healthy or diseased, whether pus or other bodily fluids are present, edema of the mucosa, etc.

In another embodiment, the device is substantially uniform in composition. In another embodiment, the device comprises of a plurality of regions that form an integrated whole. In another embodiment, the device is comprised of an interior region and a peripheral region, wherein the regions exhibit different compositions. In another embodiment, the peripheral region is formed from a biocompatible material. In another embodiment, the microstructure of the materials used with the invention is controlled in order to produce a device of controlled mechanical properties (e.g., tensile strength, elasticity). In another embodiment, the material is typically synthetic or man-made. In another embodiment, naturally occurring composition are used. In another embodiment, biocompatibility requires a material purity of a pharmaceutically acceptable grade.

In another embodiment, the material is a hydrophilic polymer. In another embodiment, the material hydrophilic polymers include polyethylene glycol, polyoxyethylene, polymethylene glycol, polytrimethylene glycols, polycinylpyrrolidones, and derivatives thereof. In another embodiment, the polymers are linear or multiply branched. In another embodiment, the material is polyethylene glycol (PEG) containing compound. In another embodiment, the material is a polyvinyl alcohol, polyacrylic acid, polyglycolic acid, polydioxanone. In another embodiment, the material is a biodegradable material such as polyesters of an α-hydroxy acids, lactic acid, glycolic acid, lactic esters, caprolactone, polyether-polyester combinations especially of polyethylene glycol (PEG) and aliphatic polyesters like poly (lactic acid), poly (glycolic acid) and poly (caprolactone), either as a blend or as a copolymer, in order to increase the hydrophilicity and degradation rate. In another embodiment, the material is a biodegradable polyanhydrides or polyorthoesters having labile backbone linkages.

In another embodiment, the material is a polysaccharide. In another embodiment, the material is hyaluronic acid. In another embodiment, the material is cyclodextrin. In another embodiment, the material is hydroxymethylcellulose. In another embodiment, the material is cellulose ether. In another embodiment, the material is a glycan. In another embodiment, the material is a collagen and other collagenic (collagen-like) materials In another embodiment, the device is used in conjunction with pharmaceutical technologies known in the art. In another embodiment, a pharmacologically active constituent is bound to the device member or may be eludable. In another embodiment, such pharmacologically active constituents may promote healing and may include, for example, antibiotics, antifungal agent, anti-inflammatory, or the like. In another embodiment, the biocompatible material may be free from any pharmacologically active constituents.

In another embodiment, the device comprises a pharmaceutical substance that treats or prevents a microbial infection, the substance delivered may comprise pharmaceutically acceptable salt or dosage form of an antimicrobial agent (e.g., antibiotic, antiviral, antiparacytic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), etc.

In another embodiment, the device is inserted for a long period of time. In another embodiment, the device remains in the nose for a long period of time. In another embodiment, the device remains in the nose for at least one year. In another embodiment, the device remains in the nose for at least two years. In another embodiment, the device remains in the nose for at least three years.

In another embodiment, the device remains in the nose for at least one year. In another embodiment, the device remains in the nose for at least a month. In another embodiment, the device remains in the nose for at least three months. In another embodiment, the device remains in the nose for at least four months. In another embodiment, the device remains in the nose for at least five months. In another embodiment, the device remains in the nose for at least seven months.

In another embodiment, the device remains in the nose for at least an hour. In another embodiment, the device remains in the nose for at least a day. In another embodiment, the device remains in the nose for at least three days. In another embodiment, the device remains in the nose for at least four days. In another embodiment, the device remains in the nose for at least a week. In another embodiment, the device remains in the nose for at least two weeks.

In another embodiment, the device is degraded at a programmed rate. In another embodiment, the device is designed to degrade at a rate wherein structure may be completely removed by aqueous solution flushing. In another embodiment, the device maintains sufficient structural integrity to maintain patency for a designed period of time. In another embodiment, the period of treatment may be for a period between two weeks, two months, six months, twelve months or more.

In another embodiment, a measure of the ability to maintain structural integrity would be that the device can sustain a radially applied force without breaking (after the defined period of time) that is at least one-half of the structural force that can be sustained prior to implantation or immersion in a test environment.

In another embodiment, it is well-known in the art that chemical materials, including lubricants, medicaments, and the like, may be dissolved or dispersed in a polymer and this will bloom or exude or migrate from the polymer for local delivery of the material.

In another embodiment, the device provides high frequency jet ventilation (HFJV) or low frequency jet ventilation (LFJV) characterized by its opening system, low tidal volume and low airway pressure. In another embodiment, the device maintains effective oxygenation and/or ventilation.

In another embodiment, provided herein a method of ventilating a subject afflicted with a pathology resulting in compromised breathing, comprising the steps of: I. within a nasal airway of the subject, positioning an apparatus for nasally delivering a jet of air comprising: an elongated flexible tube having a proximal end, a distal end, an external surface, an internal surface and a wall portion defining at least one lumen extending substantially the entire length of the tube, an opening through the external surface of the tube located dorsally adjacent the proximal end, an opening through the internal surface of the tube located dorsally adjacent the distal end and a lumen therebetween, an opening through the external surface of the tube located ventrally adjacent the proximal end, an opening through the wall portion of the tube located ventrally adjacent to the distal end and a lumen therebetween; an air jet catheter extending between the dorsally located external opening and dorsally located internal opening, the first catheter having a proximal end and a distal end, wherein the proximal end is extending from the dorsally located external opening; and a CO2 monitoring catheter extending between the ventrally located opening and wall portion opening, the second catheter having a proximal end and a distal end, wherein the proximal end is extending from the ventrally located external opening; and II. Initiating jet ventilation through the air jet catheter tube using a jet ventilator.

In another embodiment, provided herein a method of ventilating a subject afflicted with a respiratory depression, apnea, hypoxia, hypercapnia, or any combination thereof comprising the steps of: a. within a nasal airway of a subject, positioning an apparatus for nasally delivering a jet of air comprising an elongated flexible tube having a proximal end, a distal end, an external surface, an internal surface and a wall portion defining at least one lumen extending substantially the entire length of the tube, an opening through the external surface of the tube located dorsally adjacent the proximal end, an opening through the internal surface of the tube located dorsally adjacent the distal end and a lumen therebetween, an opening through the external surface of the tube located ventrally adjacent the proximal end, an opening through the wall portion of the tube located ventrally adjacent to the distal end and a lumen therebetween; a jet catheter extending between the dorsally located external opening and dorsally located internal opening, the first catheter having a proximal end and a distal end, wherein the proximal end is extending from the dorsally located external opening; and a $CO_2$ monitoring catheter extending between the ventrally located opening and wall portion opening, the second catheter having a proximal end and a distal end, wherein the proximal end is extending from the ventrally located external opening; and b. Initiating jet ventilation through the air jet catheter tube using a jet ventilator.

In another embodiment, the proximal end of the $CO_2$ monitoring catheter is capped. In another embodiment, the proximal end of the $CO_2$ monitoring catheter is cuffed. In another embodiment, the proximal end of the jet catheter is capped. In another embodiment, the proximal end of the jet catheter is cuffed.

In another embodiment, provided herein a method of ventilating a subject afflicted with a respiratory depression, apnea, hypoxia, hypercapnia, or any combination thereof comprising the steps of: a. within a nasal airway of a subject, positioning a device for nasally delivering a jet of air comprising a nasal airway unit (1) comprising: a tube (7) having a proximate end (9), a distal end (6), an anterior surface (10), and a posterior surface (11), a first tube wall (15) and a second tube wall (16) enclosing a tube lumen (8); a jet catheter (4) partially enclosed within the first tube wall (15) having proximate end (12), a distal end (5) and comprising a first jet catheter wall and a second jet catheter wall (13, 17) enclosing a jet catheter lumen (14), wherein the proximate end (12) of jet catheter extends outwards from the first tube wall (15), wherein the distal end (5) of jet catheter extends inwards from the first tube wall (15) into the tube lumen; an end-tidal $CO_2$ monitoring catheter (2), partially enclosed within the second tube wall (16) having proximate end (18), a distal end (3) and comprising a first end-tidal $CO_2$ monitoring catheter wall and a second end-tidal $CO_2$ monitoring catheter wall (19, 20) enclosing an end-tidal $CO_2$ monitoring catheter lumen (21), wherein the proximate end (18) of an end-tidal $CO_2$ monitoring catheter extends outwards from the second tube wall (16), wherein the distal end (3) of an end-tidal $CO_2$ monitoring catheter is located within the second tube wall (16); and i. Initiating jet ventilation through the jet catheter tube using a jet ventilator. In another embodiment, the proximal end of the tube is flared. In another embodiment, the proximal end of the end-tidal $CO_2$ monitoring catheter is capped. In another embodiment, the proximal end of the end-tidal $CO_2$ monitoring catheter is cuffed. In another embodiment, the proximal end of the jet catheter is capped. In another embodiment, the proximal end of the jet catheter is cuffed.

In another embodiment, the $CO_2$ monitoring catheter is an end-tidal $CO_2$ monitoring catheter.

In another embodiment, the method further comprises adjusting the position of the distal end of the jet catheter to obtain the maximum end-tidal $CO_2$ with a capnogram having a stable plateau. In another embodiment, the method further comprises observing the patient's vocal cord(s) by at least one visual monitoring means. In another embodiment, the method further comprises observing the patient's vocal cord with a fiber-optic scope.

In another embodiment, the method further comprises monitoring the chest rise and breath sound of the patient on the subject's exterior chest wall.

In another embodiment, the method further comprises shaping the jet nasal airway device within the nasal airway.

In another embodiment, the method further comprises discontinuing jet ventilation through the jet catheter. In another embodiment, the method further comprises discontinuing jet ventilation through the jet catheter, and providing ventilation to the subject through the tube. In another embodiment, the method further comprises capping the proximate end of the jet catheter. In another embodiment, the method further comprises sealing the proximate end of the jet catheter. In another embodiment, the method further comprises providing conventional ventilation to the subject through the first tube. In another embodiment, the method further comprises providing jet ventilation to the subject through the tube. In another embodiment, the method further comprises the delivery of medication to the subject through the jet catheter. In another embodiment, the method further comprises the delivery of medication to the subject through the tube. In another embodiment, the method further comprises applying suction forces to the nasal airway through the jet catheter. In another embodiment, the method further comprises applying suction forces to the nasal airway through the tube. In another embodiment, the device is controlled for pulse frequency, pulse pressure, pulse waveform, amount of air or oxygen at various concentrations per pulse, or their combination. In another embodiment, the nasal airway unit is controlled for pulse frequency, pulse pressure, pulse waveform, amount of air per pulse, or their combination.

In another embodiment, provided herein a system comprising a jet nasal airway device. In another embodiment, provided herein a system comprising a device as described herein. In another embodiment, the system further comprises a $CO_2$ level monitoring means. In another embodiment, the system further comprises a tank comprising a composition of compressed gasses. In another embodiment, the system further comprises a tank comprising compressed air. In another embodiment, the system further comprises a tank comprising a composition of compressed oxygen. In another embodiment, the system further comprises a tank comprising compressed oxygen. In another embodiment, the system further comprises an ECG. In another embodiment, the system further comprises at least one visual monitoring means. In another embodiment, the system further comprises a fiber-optic scope. In another embodiment, the system further comprises a cap fitting the proximate end of the jet catheter. In another embodiment, the system further comprises a medication delivery unit. In another embodiment, the system further comprises means providing suction.

EXAMPLES

Clinical Results of the Jet Nasal Airway

Figure 3:
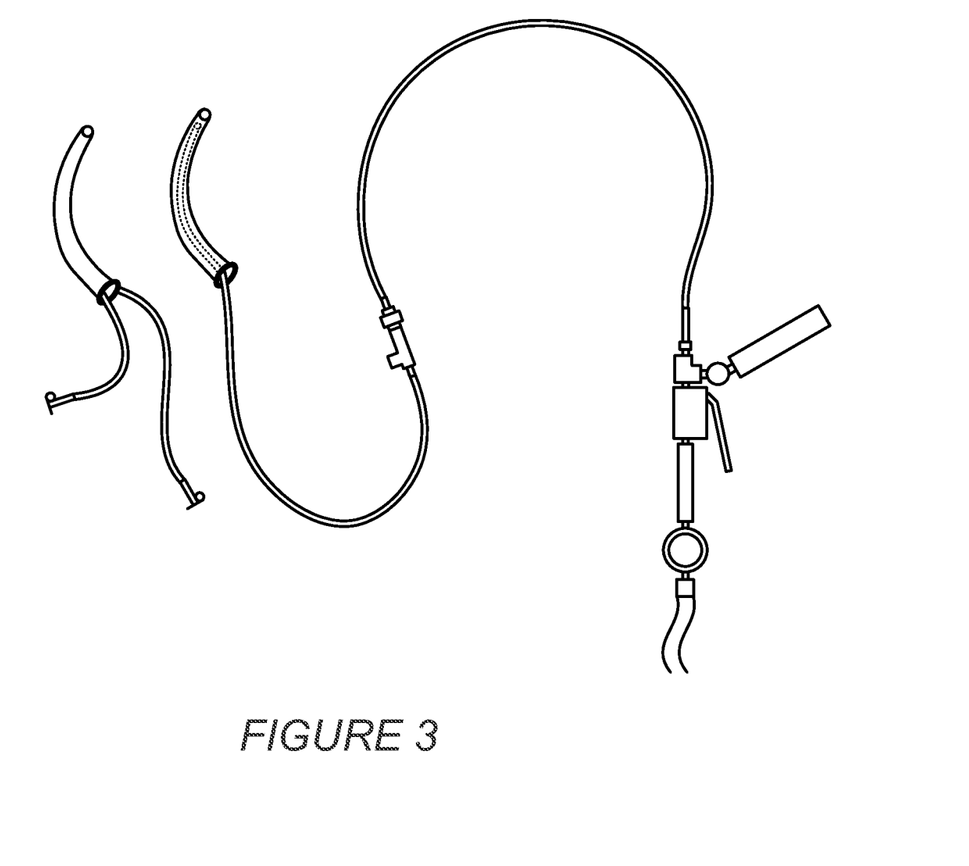
FIG. 3 illustrates a jet nasal prototype and a similar setting up using a regular nasal airway and a jet catheter inside its lumen, according to one embodiment of the invention. The nasal airway on the left side is a prototype of jet nasal airway. A jet catheter was placed in the lumen of a regular blue nasal airway on the right side, with its distal end leveled to the distal end of the nasal airway and proximal end connecting to a manual jet ventilator for performing supraglottic jet oxygenation and ventilation.

The prototype of the jet nasal airway is shown in FIG. 3. Its concept has been tested in patients using a regular nasal airway together with a suction catheter as a jet catheter connected to a Sander's manual jet ventilator (FIG. 3). The inventor of the instant application has tested the concept in at least 50 patients receiving procedures of colonoscopy, upper gastrointestinal endoscopy and endoscopic retrograde cholangiopancreatography (ERCP) under heavy sedation with the continuous intravenous infusion of propofol (100-150 mcg/kg/min).

In a preliminary study, a regular nasal airway as shown in FIG. 3 is inserted in one of the nostril in patients. A jet catheter with ID around 2 mm is placed into the lumen of the regular nasal airway with its distal end parallel to the distal end of nasal airway and proximal end connected to a manual jet ventilator. Jet ventilation was performed with respiratory rate of 15/min, driving pressure of 15 psi and I/E ration of 1:2. Patients were monitored for SaO2, heart rate, breathing rate, blood pressure and end-tidal $CO_2$ (PetCO2). The inventor has found that supraglottic jet ventilation using this setting up significantly improved oxygenation in patients under heavy sedation, with obvious chest rising and increase of $SaO_2$ to a desirable level (>96%). There were no significant complications in these patients using supraglottic jet ventilation. This work demonstrates how to use a regular nasal airway and a jet catheter in its lumen for improving oxygenation in obese patients receiving upper gastrointestinal endoscopy or colonoscopy under heavy sedation with intravenous propofol infusion.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of ventilating a subject afflicted with a pathology resulting in compromised breathing, said method comprising the steps of:
   a. providing an apparatus comprising:
      1. an elongated flexible tube having:
         i. an annular cylindrical wall defining at least one tube lumen extending substantially the entire length thereof, said cylindrical wall having external and internal surfaces and having a proximal end adapted to be positioned away from the subject's vocal cords and a distal end adapted to be positioned above the subject's vocal cords to provide persistent supraglottic jet oxygenation and ventilation (SJOV),
         ii. a first catheter lumen extending lengthwise within said cylindrical wall between said external surface and said internal surface and along a dorsal region thereof, said first lumen having a first opening through the external surface of said cylindrical wall adjacent the proximal end thereof and a second opening through the internal surface of said cylindrical wall toward the distal end thereof,
         iii. a second catheter lumen extending lengthwise within said cylindrical wall along a ventral region thereof, said second lumen having a first opening through the external surface of said cylindrical wall adjacent the proximal end thereof and a second opening through a distal face of said cylindrical wall between said internal and external surfaces, at the distal end of said cylindrical wall, and
         iv. an adaptor for connecting the proximal end of the tube lumen to conventional mechanical ventilation;
      2. a first catheter extending dorsally through said first catheter lumen, said first catheter having a proximal end extending outside of said cylindrical wall through said first opening of the first catheter lumen and having a distal end extending into said tube lumen through said second opening of the first catheter lumen; and
      3. a second catheter extending ventrally through said second catheter lumen, said second catheter having a proximal end extending outside of said cylindrical wall through said first opening of the second catheter lumen and having a distal end extending to said second opening of the second catheter lumen;

b. through one nostril of the subject, inserting the distal end of said elongated flexible tube into the subject's nasal cavity;

c. within a nasal cavity of said subject, positioning the apparatus for nasally delivering persistent SJOV;

d. initiating persistent SJOV through said first catheter or said second catheter using a jet ventilator device;

e. delivering only persistent SJOV by the apparatus to the subject; and f. while delivering persistent SJOV to the subject, monitoring the subject for $SaO_2$, heart rate, breathing rate, blood pressure, chest rise, breath sound, and/or end-tidal $CO_2$ ($PetCO_2$).

2. The method of claim 1, further comprising the step of wherein said positioning comprises positioning the apparatus to persistently deliver a jet pulse above the subject's vocal cords and directed towards the vocal cords' opening to obtain maximum end-tidal $CO_2$ with a capnogram having a stable plateau, best chest rise or breath sound.

3. The method of claim 1, further comprising the step of providing conventional ventilation using a breathing bag to said subject through the first tube lumen.

4. The method of claim 1, wherein an inner diameter of said first catheter lumen is smaller than an inner diameter of said tube lumen.

5. The method of claim 1, wherein said first catheter extends to a point adjacent to the distal end of said tube lumen.

6. The method of claim 1, whereby said first catheter lumen has an inner diameter of between 0.1 mm and 2.5 mm.

7. The method of claim 1, whereby said second catheter lumen has an inner diameter of between 0.1 mm and 2.5 mm.

8. The method of claim 1, whereby said tube lumen has an inner diameter of between 1 mm and 10 mm.

9. The method of claim 1, whereby said apparatus has a length of between 2 and 20 cm.

10. The method of claim 1, further comprising controlling the jet ventilator for jet pulse frequency, pulse pressure, inspiratory/expiratory (I/E) ratio, and oxygen concentration in a jet pulse.

11. The method of claim 10, further comprising the step of synchronizing jet pulses from the jet ventilator with spontaneous breathing of subject.

12. The method of claim 1, whereby the pathology is respiratory depression, apnea, hypoxia, hypercapnia, or any combination thereof.

13. The method of claim 1, further comprising the step of adjusting the position of the apparatus in the nasal cavity to obtain maximum end-tidal $CO_2$ or best chest rise in the subject.

* * * * *